United States Patent
Groll et al.

(10) Patent No.: US 8,465,968 B2
(45) Date of Patent: Jun. 18, 2013

(54) BIOSENSOR SYSTEM BASED ON RECOGNITION INDUCED BIREFRINGENCE (RIB)

(75) Inventors: Jürgen Groll, Oberstotzingen (DE); Martin Möller, Aachen (DE); Matthias Eberhardt, Ulm (DE)

(73) Assignee: DWI an der RWTH Aachen e.V., Aachen (DE)

( * ) Notice: Subject to any disclaimer, the term of this patent is extended or adjusted under 35 U.S.C. 154(b) by 665 days.

(21) Appl. No.: 12/645,005

(22) Filed: Dec. 22, 2009

(65) Prior Publication Data
US 2010/0167263 A1   Jul. 1, 2010

(30) Foreign Application Priority Data
Dec. 31, 2008  (EP) .................................... 08022585

(51) Int. Cl.
  *C12M 1/34*  (2006.01)
(52) U.S. Cl.
  USPC .............. 435/287.2; 422/82.11; 435/288.7; 435/808; 436/164; 436/524; 436/528; 436/531; 436/805
(58) Field of Classification Search
  None
  See application file for complete search history.

(56) References Cited

U.S. PATENT DOCUMENTS

| | | |
|---|---|---|
| 6,180,239 B1 | 1/2001 | Whitesides et al. |
| 2002/0128234 A1* | 9/2002 | Hubbell et al. ............... 514/100 |

FOREIGN PATENT DOCUMENTS

| | | |
|---|---|---|
| WO | WO2005090975 A1 | 9/2005 |

OTHER PUBLICATIONS

Abdulhalim, Ibrahim, et al. "Grating based on nanophotonic structured configurations for biosensing," Proc. of SPIE vol. 7035, 70350T, (2008).

Gauglitz, G., et al. "Chemical and biochemical sensors basedon on interferometry at thin (multi-)layers," Sensors and Actuators B, 11 (1993) 21-27.

Harsanyi, G., "Polymer films in sensor applications: a review of present uses and future possibilites," vol. 20, No. 2, (2000), pp. 98-105.

Lee, Chang-Soo, et al. "Protein patterning on silicon-based surface using background hydrophobic thin film," Biosensors and Bioelectronics 18 (2003) pp. 437-444.

Liu, Shaomin, et al. "New biosensors made of specially designed transparent chips with nano-optical tags," Smart Mater, Struct, 16 (2007) 2214-2221.

European Search Report of European Application No. EP08022585 Mar. 23, 2009 and mailed Apr. 3, 2009.

Communication under Rule 71(3) EPC dated Jan. 2, 2012, for corresponding EP Patent Application No. 08 022 585.7.

Zhian, L., et al., "Label-free biosensor by protein grating coupler on planar optical waveguides", Optics Letters, Aug. 1, 2008, pp. 1735-1737, vol. 33, No. 15, Optical Society of America.

* cited by examiner

*Primary Examiner* — Chris L Chin
(74) *Attorney, Agent, or Firm* — Pergament Gilman & Cepeda LLP; Milagros A. Cepeda

(57) ABSTRACT

The present invention relates to a label-free biosensor system, a method for manufacturing said label-free biosensor system, its use for detecting biochemical reactions and/or bindings, enzymatic reactions, nucleic acid hybridizations, protein-protein interactions and protein-ligand interactions, as well as an assay method for detecting and/or quantifying an analyte of interest in a biological sample which comprises detecting the Recognition Induced Birefringence (RIB) generated in the presence as opposed to the absence of said analyte by bringing said sample into contact with said label-free biosensor system.

10 Claims, 4 Drawing Sheets

**NCO-sP(EO-*stat*-PO)**

$M_n$ = 2 kDa / arm; m = 0.8; n = 0.2

BIOSENSOR SYSTEM BASED ON RECOGNITION INDUCED BIREFRINGENCE (RIB)

TECHNICAL FIELD

The present invention relates to a label-free biosensor system, a method for manufacturing said label-free biosensor system, its use for detecting biochemical reactions and/or bindings, enzymatic reactions, nucleic acid hybridizations, protein-protein interactions and protein-ligand interactions, as well as an assay method for detecting and/or quantifying an analyte of interest in a biological sample which comprises detecting the Recognition Induced Birefringence (RIB) generated in the presence as opposed to the absence of said analyte by bringing said sample into contact with said label-free biosensor system.

BACKGROUND

Biomolecules on solid surfaces have been investigated extensively to fabricate biosensors for a broad variety of applications. Amongst different strategies, affinity type biosensors are one of the most powerful and popular approach. Such sensors are based on the specific capabilities of a biorecognition element that is immobilized on a solid surface to selectively bind an analyte from a solution. They are versatile because they enable the determination of highly different species by selecting an appropriate biorecognition process, such as antibody-antigen interactions, complementary oligonucleotides interactions, and ligand-biological receptor interactions. One important aspect of such sensors is the minimization of non-specific binding to the sensor surface since such fouling increases the background noise, thus decreasing the signal to noise ratio and thereby the sensitivity. Detection of the signal from an analyte-biorecognition molecule complex is usually based on optical labels and probes of luminescence dye molecules. If the sensor is based on enzyme linked immunosorbent assay (ELISA) detection techniques, antibodies that are covalently linked to an enzyme such as horseradish peroxidase are used for detection. These antibodies either directly target the analyte or act as secondary antibodies to detect antibody-analyte complexes on the sensor surface. For detection of the signal, a substance is added that the enzyme can convert to a detectable signal like luminescence or fluorescence so that the amount of antigen in the sample can be determined.

Optical detection techniques, however, implicate the use of covalently labeled biomolecules if spatial resolution of the optical signal shall be accomplished. Such constructs are expensive and may restrict the assay due to difficulties in detecting certain biochemical activities. Moreover, the quantitative measurement of luminescence spectra sometimes requires complex and expensive instruments. Thus, alternative detection methods have been developed that exploit changes that either occur in the intrinsic physical property of the biomolecule itself or the interface between immobilized molecule and solid substrate as a result of its interaction with the target analyte. Such "label-free" biosensor assays are fairly straightforward, since an unlabeled biomolecule binds to an unlabeled analyte. Thus, numerous label-free biosensor systems have been developed with detection methods that make use of surface plasmon resonance (SPR), MALDI-TOF MS, electrochemical sensing, reflectometric interference spectroscopy, and quartz-crystal microbalances (QCM). Most of these label-free biosensors, however, require expensive and complicated equipments and are not straightforward to use. Moreover, sensitivity, robustness and the possibility to develop portable system are critical issues.

SUMMARY

Accordingly, the object underlying the present invention is to provide further "label-free" biosensor assays which do not require expensive and complicated equipments, but still have proper sensitivity and robustness.

The solution to the above technical problem is achieved by providing the embodiments characterized in the claims.

In particular, in a first aspect of the present invention there is provided a label-free biosensor system comprising: an anisotropically microstructured elastomeric sensor substrate having elevated regions and depressions on at least one side, wherein the distance between the elevated regions is in the range from 0.5 to 100 µm and the height of the elevated regions is in the range from 1 to 500 µm, wherein either (a) said sensor substrate is made of an elastomer, preferably a polysiloxane or a fluororesin, and is further coated, at least on the top surface thereof, with a polymeric material selected from poly(ethylene oxide), poly(propylene oxide), poly(glycidol) and copolymers thereof, said polymeric material being bound to the sensor substrate either covalently or through ionic interactions, complexes or hydrogen bridges, or (b) said sensor substrate is composed in its entirety of such a polymeric material selected from poly(ethylene oxide), poly(propylene oxide), poly(glycidol) or copolymers thereof or a hydrogel-forming polymer, and wherein, only on the elevated regions, biorecognition molecules are covalently bound via said polymeric material or directly to said sensor substrate, respectively.

A further subject matter of the present invention relates to the use of said label-free biosensor system for detecting biochemical reactions and/or bindings, enzymatic reactions, nucleic acid hybridizations, protein-protein interactions and protein-ligand interactions, complex formations and other forms of molecular recognition processes. A still further subject matter of the present invention relates to an assay method for detecting and/or quantifying an analyte of interest in a biological sample which comprises detecting the Recognition Induced Birefringence (RIB) generated in the presence as opposed to the absence of said analyte by bringing said sample into contact with the label-free biosensor system according to the present invention.

Accordingly, the present invention relates to a label-free biosensor system based on biological recognition as binding method for an analyte of interest and detection of the birefringence that is generated upon analyte binding to an anisotropically micro-structured substrate. This effect can also be called Recognition Induced Birefringence (RIB). To achieve this, a micro-structured soft sensor substrate made of an elastomer such as PDMS is coated with a polymer film that prevents unspecific adsorption but allows for covalent immobilization of the capture agent for the analyte on the top of the microstructure. Alternatively, the 2sensor substrate can be completely composed of such a polymer as mentioned above. It is also possible to use a hydrogel forming polymer for making up said sensor substrate. Such hydrogel forming polymers can be of poly(vinyl pyrrolidone), poly(alkylene glycol), poly(vinyl alcohol), poly(ethylene imine) or poly(vinyl amine) type.

Upon specific binding of the ligand/analyte, a change in surface tension results leading to a change in refractive index and thus birefringence. It has been found that on anisotropic sensor substrates as described above, this effect is strong and can be measured precisely. Without being bound thereto, these findings might be explained as follows. Since the sensor substrate is a soft polymer made of e.g. fluororesins, polysiloxanes like PDMS, said polymeric material as mentioned above or a hydrogel forming polymer, the change in surface tension leads to a force that deforms the substrate. For an isotropic substrate, the induced change in refractive index would also occur but in an isotropic way. The resulting effect would be small. Due to the anisotropy of the sensor substrate described here, the stress cannot isotropically relax. Thus, the molecular adsorption of the analyte induces a volume effect in the substrate that contributes to the signal and amplifies it. This amplification is due to the fact that few molecules at the surface can induce the change of orientation of many molecules in the elevations of the anisotropic substrate.

This anisotropic answer of the sensor-substrate volume to a change at the surface of the sensor can be detected with polarized light. A preferred method of analysis is ellipsometry.

BRIEF DESCRIPTION OF THE DRAWINGS

FIG. 1 (a) shows a PDMS sensor substrate coated by said polymer material. FIG. 1 (b) shows an example for a sensor substrate that is completely composed of said polymer material.

DETAIL DESCRIPTION

In a preferred embodiment of the present invention, the anisotropically microstructured elastomeric (soft) sensor substrate is made of PDMS (poly dimethyl siloxane). According to the present invention, the specific binding of biological molecules on anisotropically microstructured PDMS (poly (dimethylsiloxane)) substrates can be detected with high sensitivity using an ellipsometer like detection system. Ellipsometry is an optical technique for the investigation of film thickness on reflective substrates; cf. H. Arwin, Thin Solid Films 1998, 313, 764. A light beam, incident under an oblige angle onto a surface, will show reflectance and transmittance values that depend on the polarization state of the beam. This is a consequence of the light beam being an electromagnetic wave, which will interact with the electrons in the surface. The interaction will be different for electrons being moved parallel or perpendicular to the surface and it will be different depending on the binding of the electrons (dielectric or metallic behavior for example). Ellipsometers are instruments that are capable of determining the ratio of the reflectivities parallel (p) and perpendicular (s) to the surface normal. This ratio is called the ellipsometric ratio ρ, which is a complex number in general. For historical reason it is common to introduce the two angles $\Psi$ and $\Delta$ that are correlated to ρ according to equation 1:

$$\rho = \frac{R_p}{R_s} = \tan(\Psi) \cdot e^{i\Delta} \qquad \text{equation 1}$$

In the present invention, sensing is based on the anisotropic microstructure of the elastomeric substrate. Usually, the PDMS microstructures are generated according to molding procedures well known from soft lithography. A liquid mixture of PDMS prepolymer and crosslinker solution is poured onto a silicon master that has patterned relief structures. After curing of the material, the PDMS substrate can be peeled off the master structure. Since the masters can be reused indefinitely, this process is convenient and cost efficient. The technique can generate patterns and structures with feature size ranging from 0.5 μm to 500 μm. Preferably, the anisotropically microstructured elastomeric sensor substrate used has elevated regions in the form of ridges so that the depressions/grooves form channels between the ridges.

Figure 1A:
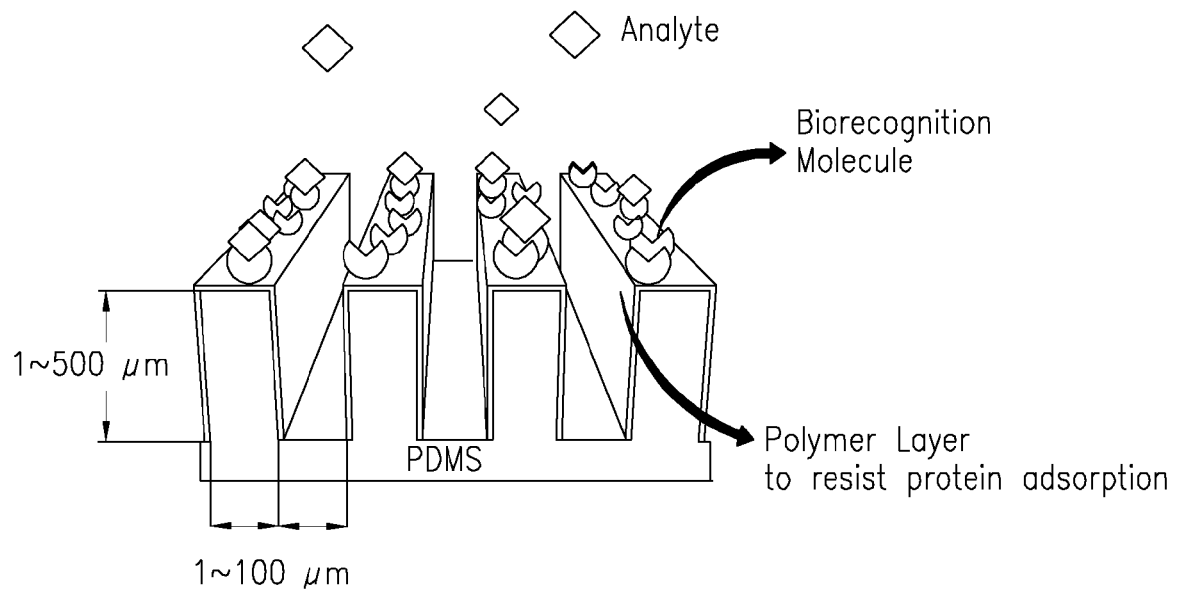
FIG. 1 shows a schematic view of an example of the anisotropically microstructured sensor substrate according to the present invention.
Figure 1B:
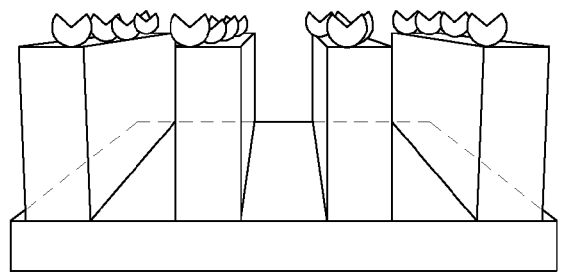
Figure 2:
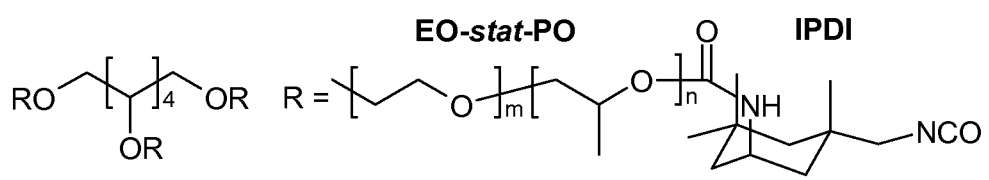
FIG. 2 shows a preferred material for the polymeric material used in the present invention, namely a specific NCO-sP(EO-stat-PO) system (PDI<1.2).

Interactions between the substrate preferably made of PDMS and biological molecules are crucial for the sensitivity of this biosensor system. In order to control these interactions, nonspecific protein adsorption on such elastomeric substrates, preferably made of PDMS, has to be prevented. Poly(ethylene oxide) (PEO) has been used extensively as a coating material to generate surfaces that resist non-specific protein adsorption. According to a preferred embodiment of the present invention, the polymeric material which is capable of resisting non-specific protein adsorption and thus being coated onto the sensor substrate, is selected from an isocyanate functionalized P(EO-stat-PO). Surely, such P(EO-stat-PO) polymers can also be functionalized by (meth)acrylate, oxirane, oxazoline, carboxylic acid, carboxylic ester, carboxylic anhydride, thiol, amine, vinyl ether, vinyl ester, Diels Alder reactive groups, alkoxysilanes, etc. Concerning such functionalized groups, it is explicitly referred to DE 102 03 937 the disclosure of which is herewith incorporated by reference concerning this specific aspect. In a specifically preferred embodiment of the present invention, the coating system, i.e. the respective polymeric material is composed of six armed star shaped molecules with a molecular weight in the range of 1 to 3 kDa, preferably about 2 kDa per arm and a polymer backbone of statistically copolymerized ethylene oxide (EO) and propylene oxide (PO) in a ratio of about 4:1, where the distal ends of the arms are functionalized with reactive isocyanate (NCO) groups (NCO-sP(EO-stat-PO); see FIG. 2. Those polymers are known in the art; cf. DE 102 03 937. These coatings have been shown to combine prevention of unspecific interaction with high functionality; cf. Gasteier et al., Macromol. Biosci. 2007, 7, 1010-1023. Furthermore, these coatings can be applied to elastomeric PDMS substrates in an easy manner. However, other star shaped molecules like those disclosed in EP 1 864 777 can also be employed in the present invention.

Generally, surface modification of PDMS is difficult because the material is inert. In a preferred embodiment of the present invention, ammonia plasma is used to generate amino functionalized PDMS surfaces being capable of undergoing a covalent urea-bridging with isocyanate functionalities. Spin coating of aqueous NCO-sP(EO-stat-PO) solutions onto amino functionalized PDMS substrates provides precise control of the layer thickness via rotation speed and prepolymer concentration and results in homogeneous layers. Furthermore, the NCO-sP(EO-stat-PO) layers can be functionalized by the reaction between the isocyanate groups in freshly prepared layers and biorecognition molecules selected from the group consisting of peptides, proteins, antibodies, antibody fragments, lectins, carbohydrates, DNA, oligonucleotides, aptamers, low molecular weight ligands such as biotin, complexing agents and polyionic tags. Preferably, these biorecognition molecules (capture molecules) have amino or alcohol functionalities. However, the present invention allows functionalization with a big variety of molecules such as low molecular weight ligands, peptides, oligonucleotides, carbohydrates, and whole proteins such as antibodies or lectins.

In accordance with the present invention, the biorecognition molecules are covalently bound to said multifunctionalized polymeric material on the elevated regions of the sensor substrate.

The present invention also relates to a method of manufacturing said label-free biosensor system, comprising the steps of:

(i) providing an anisotropically microstructured sensor substrate having elevated regions and depressions on at least one side, wherein the distance between the elevated regions is in the range from 0.5 to 100 µm and the height of the elevated regions is in the range from 1 to 500 µm, (ii) optionally functionalizing said sensor substrate to generate functional groups on the surfaces of said sensor substrate, and coating said thus functionalized sensor substrate with the polymeric material, thereby causing covalent bonding or ionic interactions, complexes or hydrogen bridges between the surface of said sensor substrate and said polymeric material, and (iii) functionalizing said sensor substrate provided in step (i) or obtained in step (ii) only on the elevated regions of said sensor substrate with biorecognition molecules via covalent bonding to said polymeric material or to said sensor substrate, respectively.

Figure 3:
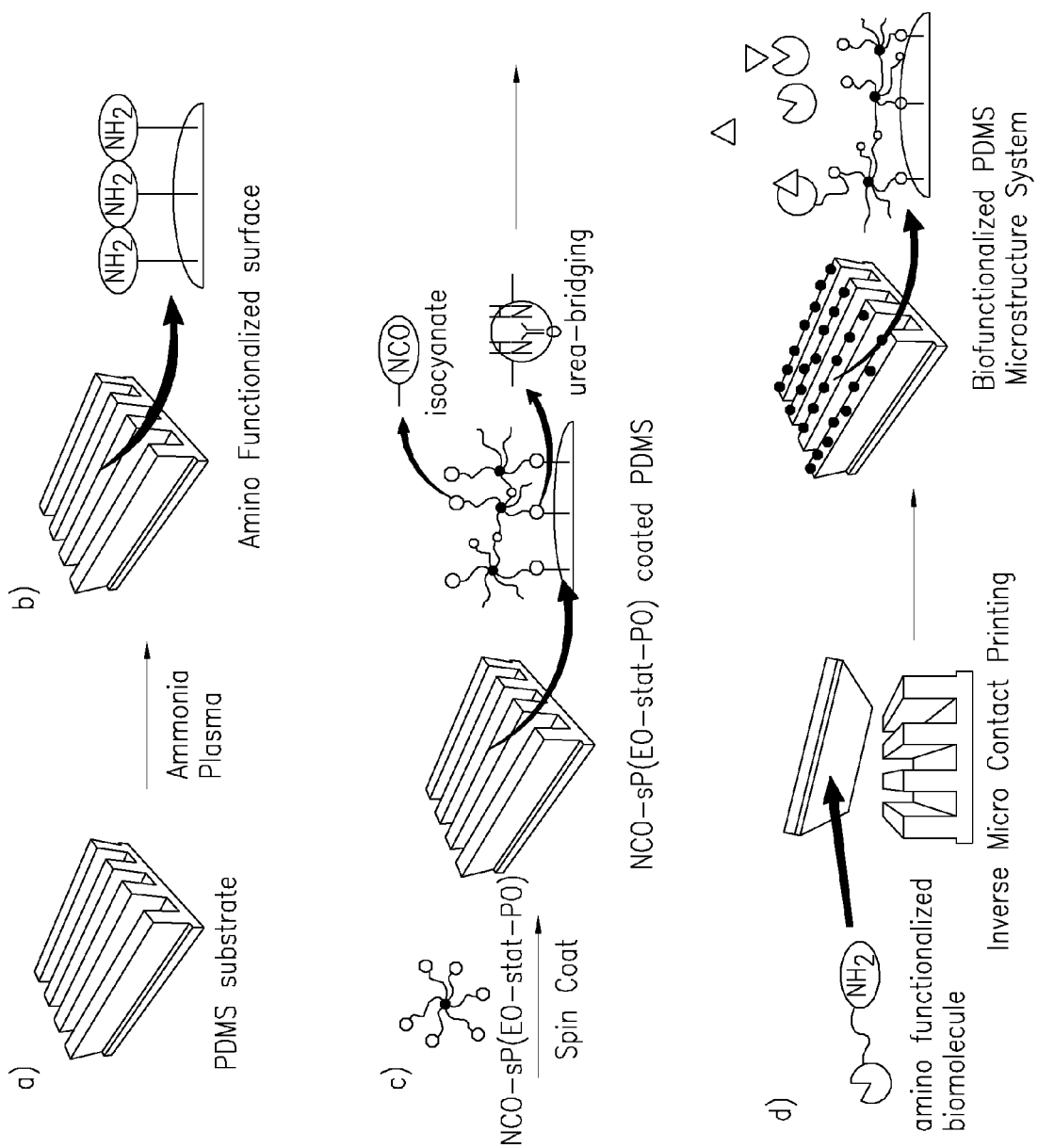
FIG. 3 shows an overview on the workflow for manufacturing a sensor substrate with NCO-sP(EO-stat-PO) as an example of the present invention.

Using this approach, the biofunctionalized microstructure as shown in FIG. 3d can preferably be obtained by an inverse microcontact printing (µCP) process. µCP is a technique that uses the relief pattern on the surface of a PDMS stamp to form patterns on substrates by wetting of the PDMS stamp with the molecule of interest and transferring the pattern through contact between the stamp and the substrate. Usually, a flat surface is wetted with the capture agent for the analyte and a freshly coated microstructured sensor substrate is brought into contact to transfer and covalently bind the molecules only on the elevations of the structure.

Figure 4:
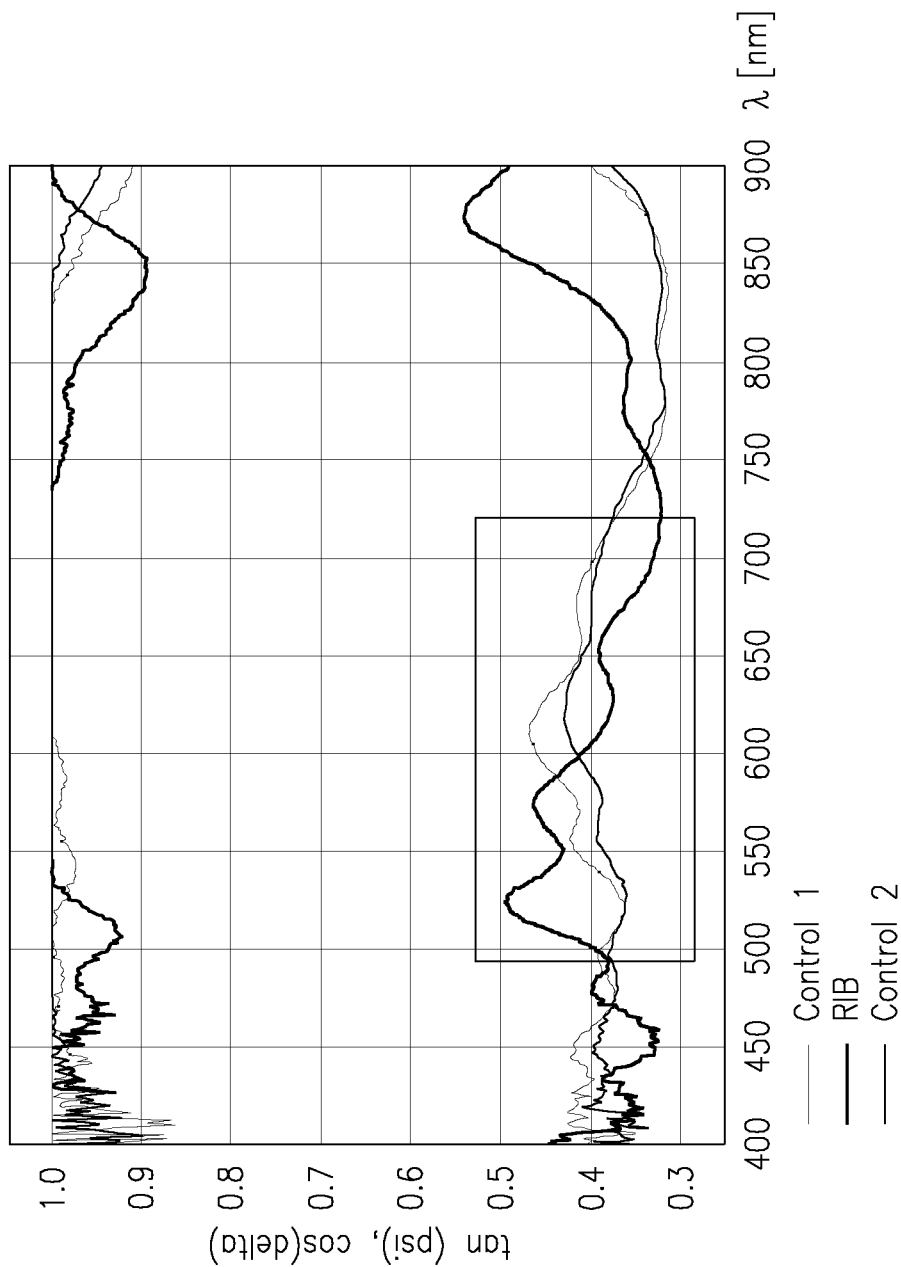
FIG. 4 shows the spectra of a biotin functionalized sensor substrate according to the present invention after incubation with streptavidin solution (black line). The red and green lines show incubated reference sample without biotin on the sensor as control.

When such a sensor substrate is immersed into a solution that contains an analyte of interest, specific adsorption of the analyte only takes place on the elevations of the structure. FIG. 4 shows results of measurements that have been performed on a sensor substrate that was functionalized with biotin as binding ligand after (black line) incubation with streptavidin solution and subsequent rinsing. A remarkable change in the wavelength of the spectrum was observed in comparison to the 2 control samples without biotin on the sensor substrate (green and red line). The PDMS sensor substrate was structured with lines of 10 µm width in a distance of 5 µm and a height of 2 µm.

If a molecule interacts with the sensor surface there are several possibilities how this is "seen" by the ellipsometer. Conventionally, the increase of the layer thickness can directly be measured. This will however result in a very tiny effect in contradiction with the comparably large effect being seen in measurements like those exemplified in FIG. 4. An explanation for the large change in wavelength is a change of the stress induced birefringence of the "stripe structure". Upon binding of the analyte, the surface tension changes on the elevations of the structured sensor while it remains unaltered in the grooves. Due to the anisotropy of the substrate, the stress cannot relax isotropically. Because of the material being a polymer where the surface effect can couple to the polymer chains this induces the change of orientation of many molecules in the elevations of the anisotropic substrate what can lead to comparably large effects. This effect can be called Recognition Induced Birefringence (RIB). However, another explanation is still possible. If an elongated structure with a different dielectric constant is immersed into another substance the elongated structure shows a phenomenon known as form birefringence. This can be utilized in polarization microscopy to show structures that are much smaller than the wavelength of light, for example microtubuli in cells.

Since differences in wavelength can be measured easily with high precision, binding of the ligand/analyte can be detected with high sensitivity. Based on respective measurements and with the estimation that one ligand molecule is present per 4 nm$^2$ at the elevations of the microstructure, a detection limit of the sensors according to the present invention can be estimated in the range of a hundred pikomol for ligand-analyte interactions with a dissoziation constant of $10^{-9}$ M which is a typical value for antibody antigen interaction.

Hence, the RIB-biosensor according to the present invention combines several important advantages such as high sensitivity, label free detection, inexpensive sensor-substrates as well as robust and straightforward to use detection hardware.

The invention claimed is:

1. Label-free biosensor system comprising:
an anisotropically microstructured elastomeric sensor substrate having elevated regions and depressions on at least one side, wherein the distance between the elevated regions is in the range from 0.5 to 100 µm and the height of the elevated regions is in the range from 1 to 500 µm, wherein either (a) said sensor substrate is made of an elastomer, and is further coated, at least on the top surface thereof, with a polymeric material selected from poly(ethylene oxide), poly(propylene oxide), poly(glycidol) and copolymers thereof, said polymeric material being bound to the sensor substrate either covalently or through ionic interactions, complexes or hydrogen bridges, or (b) said sensor substrate is composed in its entirety of a polymeric material selected from poly(ethylene oxide), poly(propylene oxide), poly(glycidol) or copolymers thereof or a hydrogel-forming polymer, and wherein, only on the elevated regions, biorecognition molecules are covalently bound via said polymeric material or directly to said sensor substrate, respectively.

2. The label-free biosensor system according to claim 1, wherein the anisotropically microstructured elastomeric sensor substrate is made of poly dimethyl siloxane.

3. The label-free biosensor system according to claim 2, wherein the PDMS, is amino functionalized poly dimethyl siloxane.

4. The label-free biosensor system according to claim 1, wherein the anisotropically microstructured elastomeric sensor substrate in its entirety is made of polytheylene oxide-stat-polypropylene oxide.

5. The label-free biosensor system according to claim 1, wherein the polymeric material for coating the anisotropically microstructured elastomeric sensor substrate is a polytheylene oxide-stat-polypropylene oxide.

6. The label-free biosensor system according to claim 5, wherein the polymeric material is made of six armed star shaped molecules with a molecular weight in the range of 1 to 3 kDa per arm and a polymer backbone of statistically copolymerized ethylene oxide (EO) and propylene oxide (PO) in a ratio 4:1, where the distal ends of the arms are functionalized with reactive isocyanate (NCO) groups.

7. The label-free biosensor system according to claim 5, wherein the polytheylene oxide-stat-polypropylene oxide is a star shaped polytheylene oxide-stat-polypropylene oxide.

8. The label-free biosensor system according to claim 1, wherein the polymeric material is multifunctionalized, and wherein the biorecognition molecules are selected from the group consisting of peptides, proteins, antibodies, antibody fragments, lectins, carbohydrates, DNA, oligonucleotides, aptamers, low molecular weight ligands, complexing agents and polyionic tags, covalently bound to said multifunctionalized polymeric material on the elevated regions of the sensor substrate.

9. The label-free biosensor system according to claim 1, wherein the elevated regions are in the form of ridges so that the depressions form channels between the ridges.

10. The label-free biosensor system of claim 1 wherein said elastomer is a polysiloxane or a fluororesin.

* * * * *